United States Patent [19]
Puel et al.

[11] Patent Number: 5,845,237
[45] Date of Patent: Dec. 1, 1998

[54] PROCESS FOR DETERMINING THE VALUE OF A PHYSICAL QUANTITY

[75] Inventors: Cécile Puel, Irigny; François Hartmann, Lyons; Claude Alain Saby, Bron, all of France

[73] Assignee: Elf Antar France, Courbevoie, France

[21] Appl. No.: 778,721

[22] Filed: Dec. 27, 1996

[30] Foreign Application Priority Data

Dec. 28, 1995 [FR] France ................................ 95 15672

[51] Int. Cl.$^6$ ........................................ G06F 17/50
[52] U.S. Cl. ...................... 702/179; 702/85; 702/189; 395/20
[58] Field of Search .............. 364/550, 551.01, 364/554, 552, 570, 581, 496–498, 578; 395/1, 10, 20, 21, 902, 903, 906; 702/57, 81–84, 85, 179, 189

[56] References Cited

U.S. PATENT DOCUMENTS

| | | | |
|---|---|---|---|
| 5,446,681 | 8/1995 | Gethner et al. | 364/554 |
| 5,455,773 | 10/1995 | Frey | 364/552 |
| 5,479,361 | 12/1995 | Kurtzberg et al. | 364/552 |
| 5,532,943 | 7/1996 | Asano et al. | 364/555 |
| 5,592,402 | 1/1997 | Beebe et al. | 364/578 |
| 5,602,755 | 2/1997 | Ashe et al. | 364/498 |
| 5,621,861 | 4/1997 | Hayashi et al. | 395/23 |
| 5,680,321 | 10/1997 | Helmer et al. | 364/499 |
| 5,699,269 | 12/1997 | Ashe et al. | 364/499 |

*Primary Examiner*—James P. Trammell
*Assistant Examiner*—Craig Steven Miller
*Attorney, Agent, or Firm*—Oblon, Spivak, McClelland, Maier & Neustadt, P.C.

[57] ABSTRACT

Process for determining the value of a physical quantity for a product to be analysed on the basis of the values of recordings of signals delivered by at least one measuring instrument fed with the said product and of a validated model, constructed from an initial file of numerical data, furthermore consisting in distributing the numerical data of the initial file into sub-groups which are homogeneous and representative in relation to one another and with respect to the said initial file. The process of the invention finds its application especially in the petroleum, chemical and food industries.

5 Claims, 4 Drawing Sheets

PROCESS FOR DETERMINING THE VALUE OF A PHYSICAL QUANTITY

FIELD OF THE INVENTION

The present invention relates to a process for determining the value of a physical quantity for a product to be analysed on the basis of the recordings of the values delivered by at least one measuring instrument fed with the said product and of a validated mathematical model.

It finds its application in control laboratories, research laboratories, production units and manufacturing units in the petroleum, chemical, petrochemical, pharmaceutical, cosmetological and food industries.

STATE OF THE PRIOR ART

A known method of determining a physical quantity for a product to be analysed consists in executing the following steps:

recording the data delivered by a measuring instrument, for example a spectrometer, fed successively with a plurality of products of which the value of the physical quantity is known. All these recordings being regarded as a set of observations, they constitute a file of initial data, constructing, from a learning file extracted from the initial file, a model which establishes a mathematical relationship between the data delivered by the measuring apparatus and the physical quantity, validating the model on the basis of a test file extracted from the initial file, applying the model for the data delivered by the measuring instrument fed with a product for which it is wished to determine the physical quantity.

The quality of this model depends on the degree of homogeneity and representativity of the test file in relation to the learning file. A method of improving the quality of the model, during the step of distributing the initial file into two sub-sets: learning and test, is known by the name of the "Kennard and Stone" algorithm.

It is described in a scientific article, R. W. Kennard and L. A. Stone, *Computer Aided Design of Experiments*, 11 TECHNOMETRICS 137–148 (February 1969).

According to this method, all the observations are regarded as being candidates for the test file. The observations are chosen sequentially in such a way that the distribution thus created is uniform in the space of the variables.

The two most remote observations are selected first. The succeeding ones are chosen one after the other as the closest to the observations previously selected, in the sense of the euclidian distance.

In this way three quarters of the observations are selected to form a learning file, the remainder constituting the test file.

This method has the characteristic of favouring the extreme data and of being sensitive to particular observations, this having the effect of falsifying the values of the physical quantity evaluated by the model. This drawback is particularly unacceptable when the quantity to be determined is used to run a unit for manufacturing the product.

BACKGROUND OF THE INVENTION

The objective of the present invention is precisely to remedy these drawbacks and provide knowledge regarding the density, shape and orientation of the sub-groups of observations, which determine the quality of the modelling.

Moreover, the invention makes it possible to optimize the distribution according to a strategy based on this quality.

For these purposes, the invention proposes a process for determining the value of a physical quantity for a product to be analysed on the basis of the values of recordings of signals delivered by at least one measuring instrument fed with the said product and of a validated model, constructed from an initial file of numerical data obtained previously from the values of the recordings of the signals delivered by the measuring instrument fed with a plurality of products and from the known values of the physical quantity for each of the said products, furthermore consisting in distributing the numerical data of the initial file into sub-groups which are homogeneous and representative in relation to one another and with respect to the said initial file.

According to another characteristic the process of the invention includes the steps consisting in:

submitting the numerical data of the initial file to a mathematical transformation, choosing a number of sub-groups greater than or equal to two, choosing the size of each of the said sub-groups, generating one or more initial distributions of the numerical data among the said sub-groups, evaluating the quality of the initial distribution or distributions of the numerical data into sub-groups on the basis of at least one quality criterion, choosing the distribution to be modified in the next step in the case of a plurality of initial distributions, generating a new distribution by modifying the distribution of the numerical data among the sub-groups according to an optimization technique, evaluating the quality of the new distribution on the basis of the quality criterion or criteria, iteratively repeating the three previous steps until satisfaction of a stopping criterion obtained by comparing the value of the quality of the last distribution with a fixed threshold or until the number of iterations reaches a fixed maximum number.

According to another characteristic of the invention, the quality criterion consists of at least one criterion chosen from the following:

criterion of representativity of the numerical data of the sub-groups with respect to the measured quantity, which employs a metric characterizing a distance between the sub-groups, criterion of homogeneity serving to compare between them on the one hand the shapes and on the other hand the orientations of the sub-groups, criterion of homogeneity serving to compare between them the densities of the numerical data in the sub-groups.

According to another characteristic of the invention, the optimization technique consists of at least one method chosen from the following:

method which employs at least one genetic algorithm, method which employs at least one neural network, method which employs at least one simulated annealing algorithm, incremental method, method which employs at least one matrix criterion of optimality, and iterative method of the bootstrap type.

According to another characteristic of the process the choice of the size of the sub-groups is optimized by applying a method of iterative optimization of a quality criterion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1A:
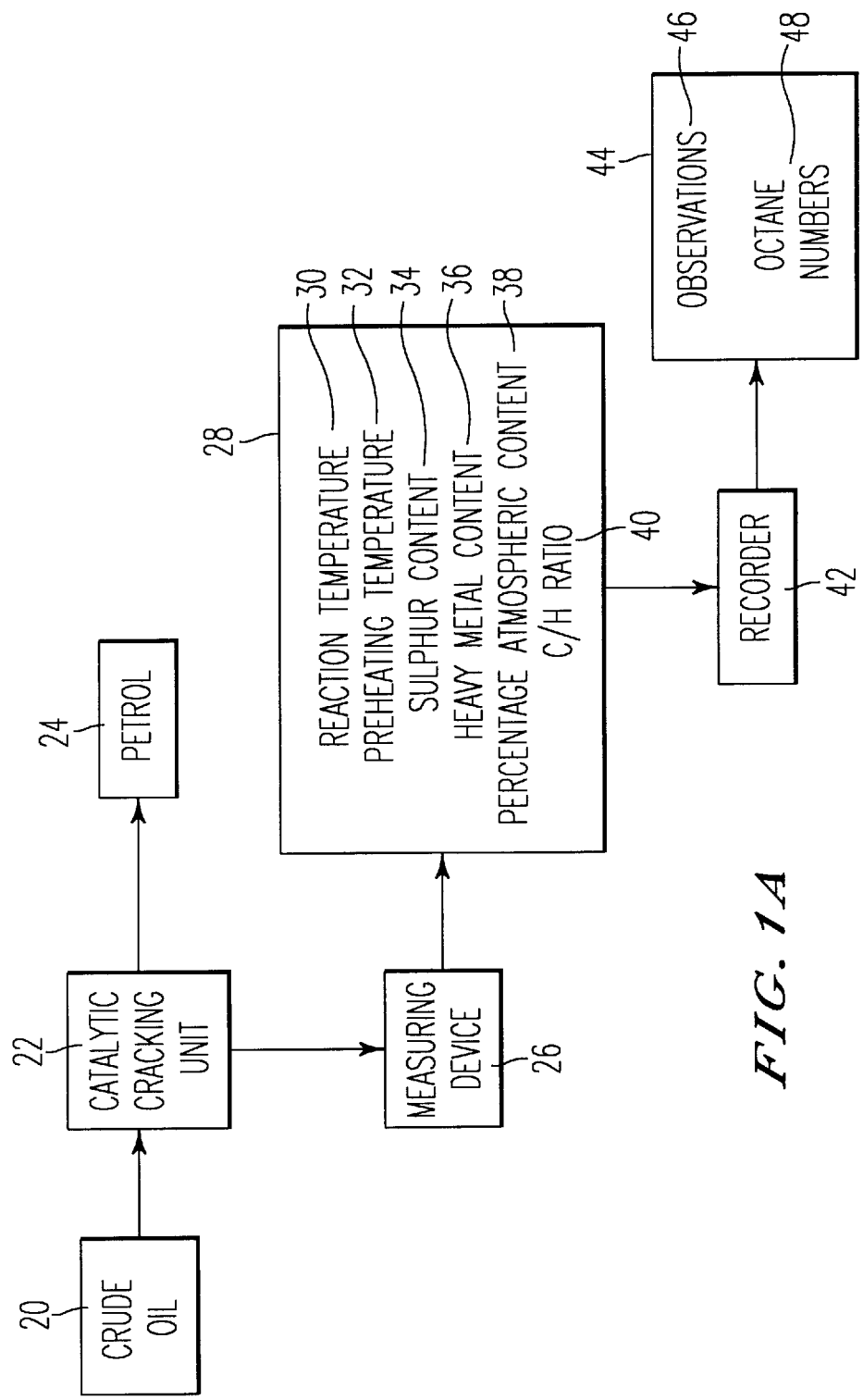
FIG. 1A is a flow diagram showing an exemplary flow of crude oil through a catalytic cracking unit, with measurements taken to obtain observations relating to octane numbers.

Referring now to the drawings, wherein like reference numerals designate identical or corresponding parts through the several views, and more particularly to FIG. 1A thereof, a crude oil refinery catalytic cracking unit 22 is shown to illustrate the environment of at least one embodiment of the present invention.

In a general manner the process of the invention is used to determine the value of a physical quantity for a product on the basis of the values of recordings of signals delivered by at least one measuring instrument.

Figure 1B:
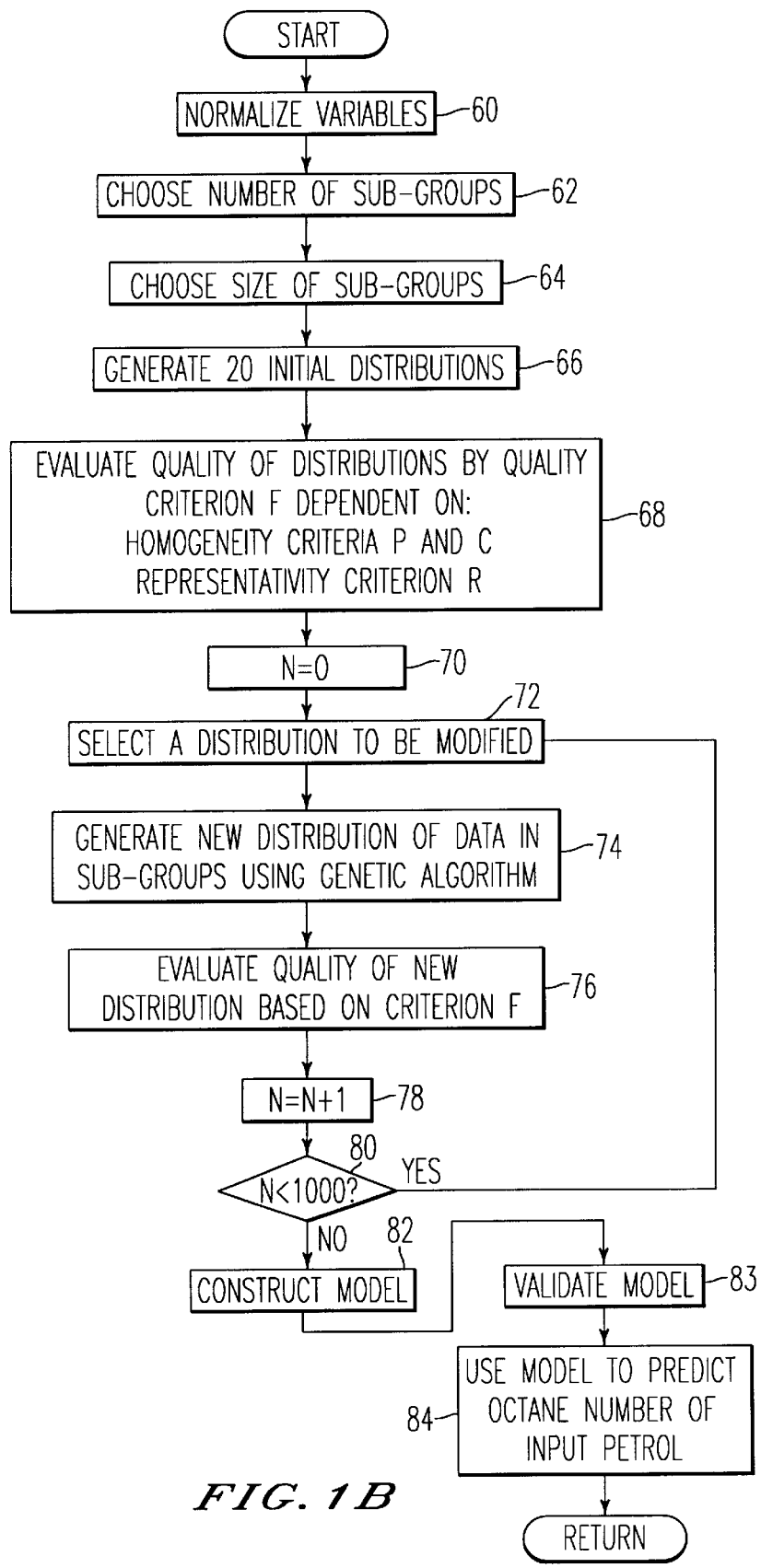
FIG. 1B is a flowchart showing logical flow for processing the observations from the catalytic cracking unit to create a model for predicting the octane number of fuel.

According to a particular mode of use, as shown in FIGS. 1A–1B, the process of the invention serves to determine the motor octane number of a fuel stemming from a catalytic cracking unit 22 in a crude oil refinery. According to this particular embodiment, crude oil 20 is fed to the catalytic cracking unit 22, as a step in production of petrol 24. A measuring device 26 measures the values recorded over several days of six variables, representative of the operating conditions of the catalytic cracking unit 22 and of analytic data characterizing the charge, namely:

the reaction temperature 30, the preheating temperature 32, the sulphur content 34, the heavy metal content 36, the % of atmospheric residue 38, the C/H ratio 40.

The six variables noted on one day constitute an observation 28. For each observation 28 the value of the octane number of the petrol 24 produced, determined by direct laboratory measurement, is recorded by a recorder 42.

The initial file 44 contains the recordings of 144 observations 46 and the corresponding values of the octane number 48 of the petrol produced.

Referring now to FIG. 1B, the next step 60 consists in centring and reducing each of the variables so as to normalize them.

Next, a number of sub-groups equal to 3 is chosen in step 62 to constitute a learning sub-group, a selection sub-group and a validation sub-group.

In order to obtain accuracy sufficient for the validity of the model in step 64, the size of the selection and validation sub-groups is fixed at 25 and 24 observations respectively, while retaining sufficient observations for the learning sub-group, namely 95 in our example.

In step 66, a set of 20 initial distributions of the data of the initial file is generated and then in step 68 the quality of these 20 initial distributions is evaluated by means of an overall quality criterion F dependent on two homogeneity criteria P and C and on a representativity criterion R.

The criterion R defines a distance between two sub-groups according to the MAHALANOBIS metric. It is calculated for each pair of learning and selection sub-groups, according to the following formula:

$$R(lea, sel) = \frac{D_T - D(lea - sel)}{D_T}$$

In which,

R(lea, sel) is a representativity criterion between the learning and selection sub-groups, $D_T$ is the MAHALANOBIS distance for a Fisher law.

D(lea, sel) is the theoretical MAHALANOBIS distance between the two learning and selection sub-groups.

R is interpreted as follows:

if R=0 the two sub-groups are not representative of one another, if R=1 the two sub-groups are merged, the closer the value of R gets to 1 the more representative of one another are the two sub-groups, conversely the nearer R is to 0, the less representative of one another are the sub-groups.

The criterion P is determined by the following formula:

$$P(app, sel) = \left[ \sum_{j=1}^{k} S_{app}(j) \cdot S_{sel}(j) \right] / \sqrt{\sum_{j=1}^{m} S_{app}^2(j) \cdot \sum_{j=1}^{m} S_{sel}^2(j)}$$

In which:

P(lea, sel) is a criterion of homogeneity of the learning and selection sub-groups, $S_{lea}$ is the sum of the eigenvectors, weighted by the eigenvalues of the learning sub-group, $S_{sel}$ is the sum of the eigenvectors, weighted by the eigenvalues of the selection sub-group, m is the number of variables equal to 6, k is the number of significant eigenvalues of the variance-covariance matrices for the learning and for the selection, P is interpreted as follows:

if P=0 the two sub-groups are not homogeneous, if P=1 the two sub-groups have the same spread in space, the nearer the value of P is to 1 the more homogeneous are the sub-groups, the nearer the value of P is to 0 the less homogeneous are the sub-groups, P expresses the spatial distribution of the data by comparing the shapes and orientations of the sub-groups. It has been determined experimentally that if P<0.7 the two sub-groups are not homogeneous.

The criterion C is determined by the following formula:

$$C(lea, sel) = \exp[-M(lea, sel)/[(n_{lea}-1)+(n_{sel}-1)]]$$

in which:

C(lea, sel) is a criterion of homogeneity of the learning and selection sub-groups, $n_{lea}$ is the number of observations in the learning sub-group, $n_{sel}$ is a number of observations in the selection sub-group, M(lea, sel) is itself defined by the formula, $$M(\text{app, sel}) = \nu[(n_{app}-1)\cdot\log|A_{app}^{-1}\cdot A| + (n_{sel}-1)\log|A_{sel}^{-1}\cdot A|]$$

in which:

|.| is a determinant.

$$\nu = 1 - \frac{2p^2 + 3p - 1}{6(p+1)} \left( \frac{1}{n_{app}-1} + \frac{1}{n_{sel}-1} - \frac{1}{n_{app}+n_{sel}-2} \right)$$

and in which:

p is the number of variables equal to 6.

$A_{lea}$ is the variance-covariance matrix of the learning sub-group, $A_{sel}$ is the variance-covariance matrix of the selection sub-group, A is the variance-covariance matrix of the set of observations of the two learning and selection sub-groups.

C is interpreted as follows:
  if C=0 the covariances of the learning and selection sub-groups are different,
  if C=1 the covariances of the learning and selection sub-groups are equal,
  the closer the value of C is to 1 the closer are the covariances and the more homogeneous the groups,
  the closer the value of C is to 0 the less homogeneous are the groups.

The overall quality criterion F is calculated as follows:
  if P<0.7 then F=0.1 P,
  if P≥0.7 then $F = 1^F = \sqrt{(P^{2+C^{2+R^{2}}/3})}$ A value of F near to 1 indicates that the three sub-groups are homogeneous and representative.

Step 70 initializes an iteration counter N to zero. The distribution to be modified in the next step 72 is chosen according to a probability proportional to the quality of each of the distributions.

A new distribution is generated in step 74 by modifying the distribution of the numerical data in the sub-groups via a method which employs a genetic algorithm. The latter is based on representing the three sub-groups as three chromosomes composed of a string of integers corresponding to the serial number of the observation in the initial file.

The distributions are optimized by alternately applying mutations and reproductions.

The quality of the new distribution is evaluated in step 76 on the basis of the criterion F defined earlier.

Step 70 adds a value of 1 to the iteration counter N. Step 80 determines whether the number of iterations is less than 1000. If the number of iterations is determined to be less than 1000, then flow proceeds to step 72. If the number of iterations is not less than 1000, then step 82 constructs a model as described below.

An overall quality criterion for the distribution, F equal to 0.98, is then obtained. This value very close to 1 indicates that the three sub-groups are homogeneous and representative, and demonstrates the attraction of the process of the invention.

If the value of F is calculated while using the Kennard and Stone method with the same set of variables we obtain F=0.05.

This very small value of F, near to zero, demonstrates that the Kennard and Stone method does not satisfy the desired homogeneity and representativity criteria.

The modelling is carried out with a multilayer neural network according to a known method according to which:

the learning sub-group serves to determine the connection weights for the neural network, the selection sub-group serves to select the right architecture and the right parameters for the algorithm, the validation sub-group serves to calculate the capacity for generalization.

Step 83 validates the model. The fit of the model to reality is expressed through the prediction standard deviation obtained over each of the sub-groups.

We find:
  for the learning sub-group: 0.25 octane number unit,
  for the selection sub-group: 0.30 octane number unit,
  for the validation sub-group: 0.25 octane number unit.

With the distribution of the sub-groups satisfying the criteria of homogeneity and representativity, the fact that these three values are close to one another shows that the modelling is of good quality.

To predict the value of the motor octane number of the petrol 24 produced at a given instant by the catalytic cracking unit 22, use is made of the model thus established in step 84, the input data being the values of the six variables representing the operating conditions and the characteristics of the charge, at the instant considered. The value of the octane number thus predicted can be used by the operator to run the unit manually or as input data to an automation program which provides for the automatic running of the unit.

Figure 2A:
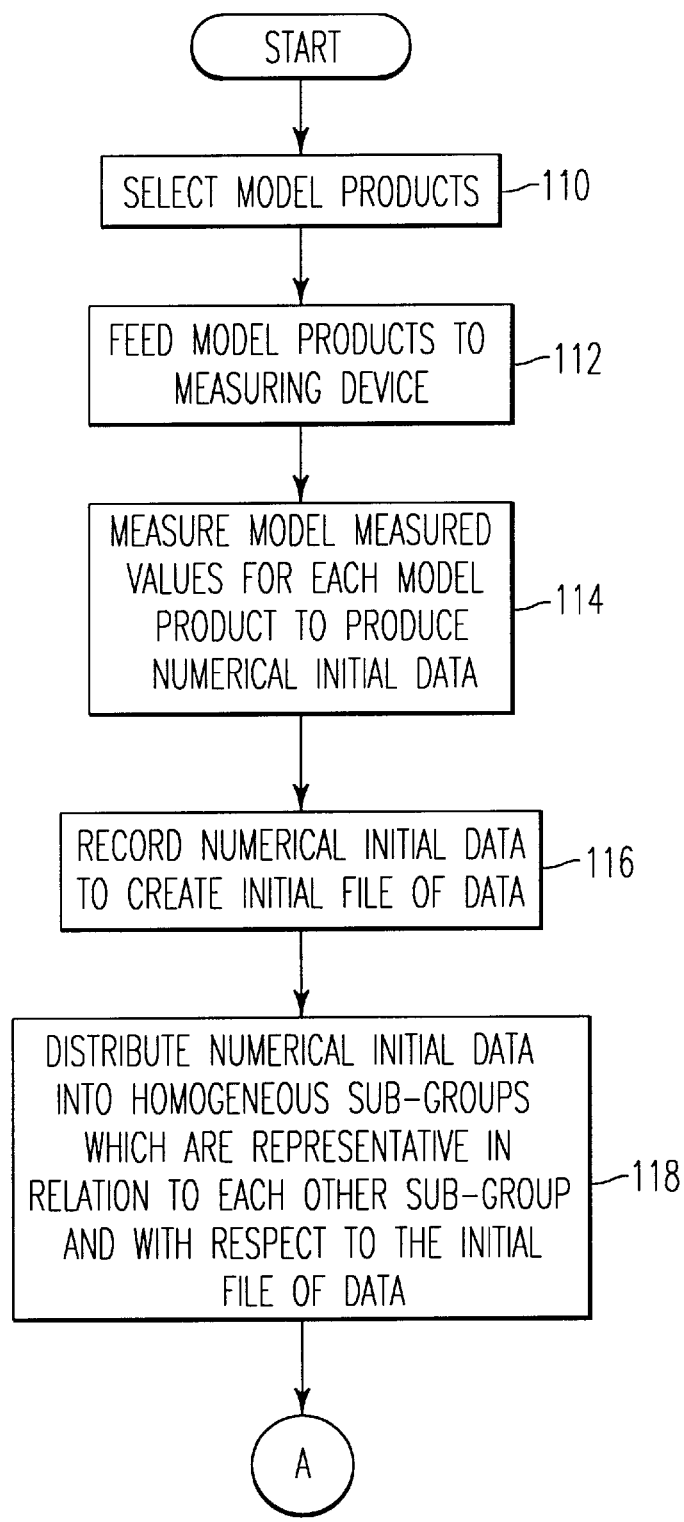
FIGS. 2A–2B are a flowchart showing the logical flow of the process of the present invention.

FIG. 2A is a flowchart showing the logical flow of the process of the present invention which is used to determine the value of a physical quantity for a desired product on the basis of values of recordings of signals delivered by at least one measuring instrument. After starting, step 110 selects a plurality of model products for which corresponding values of the physical quantity are known. Step 112 then feeds the plurality of model products to at least one measuring device. Step 114 then measures model measured values for each model product which has been fed to the at least one measuring device to produce numerical initial data. Step 116 records the numerical initial data produced by the measuring device to create an initial file of data.

Step 118 distributes the numerical initial data in the initial file of data into homogeneous sub-groups which are representative in relation to each other sub-group and with respect to the initial file of data. Flow then proceeds to step 120 of FIG. 2B.

Figure 2B:
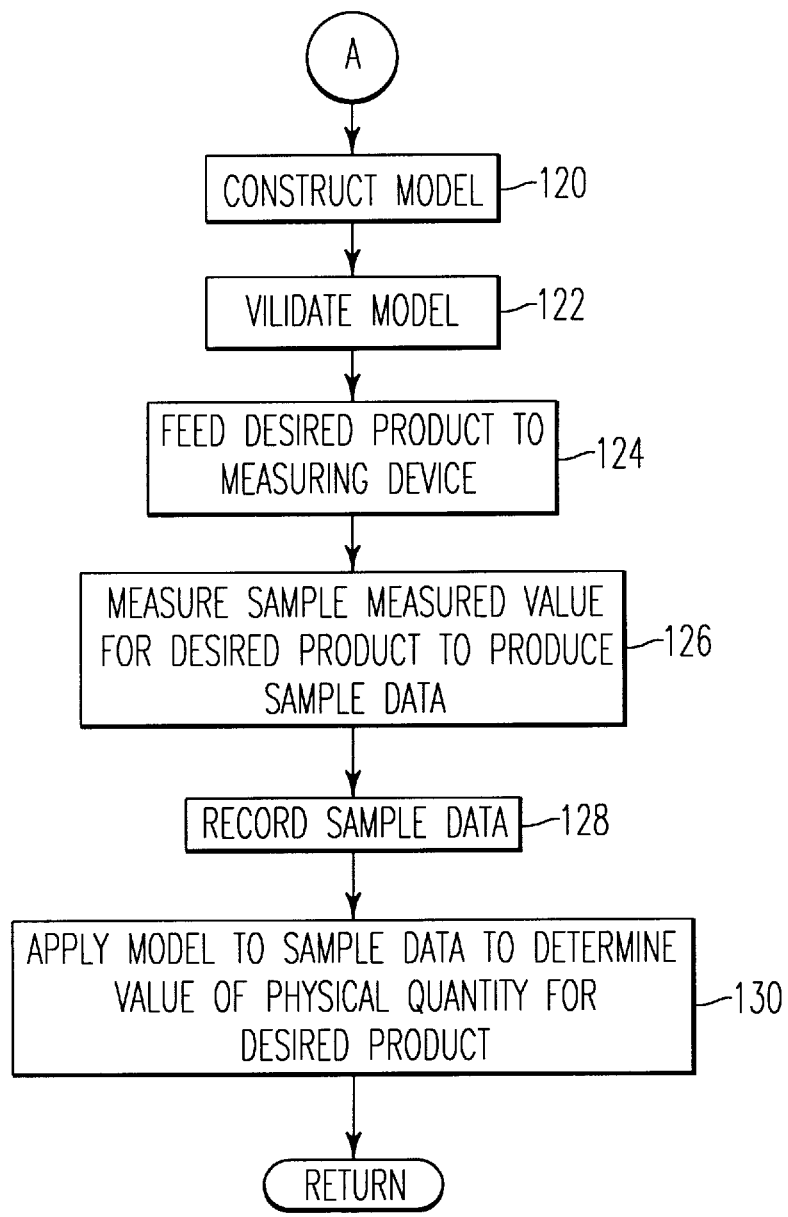

Step 120 of FIG. 2B constructs a model which establishes a mathematical relationship between the numerical initial data and the corresponding value of the physical quantity which is known for each of the plurality of model products fed to the measuring device. Step 122 then validates the model.

Step 124 feeds the desired product, for which a value of the physical quantity is desired, to the at least one measuring device. Step 126 measures a sample measured value for the desired product which has been fed to the at least one measuring device to produce sample data. Step 128 then records the sample data. Step 130 then applies the model to the sample data to determine the value of the physical quantity for the desired product. Control is then returned to the user of the process of the present invention.

The mode of use of the process of the invention which has just been described is given by way of non-limiting example. The process of the invention can be used to predict the values of very diverse physical quantities which enter into the running of manufacturing processes, on the basis of a model and recordings of signals delivered by instruments for measuring physical parameters or by analysers, especially infrared spectrometers.

We claim:

1. A process for determining the value of a physical quantity for a desired product comprising the steps of:

successively feeding at least one measuring device with a plurality of model products for which corresponding values of said physical quantity are known;

successively measuring a plurality of model measured values of said physical quantity on said at least one measuring device for said plurality of model products to produce numerical initial data;

recording said numerical initial data to create an initial file of data;

distributing said numerical initial data into a plurality of sub-groups which are homogeneous and have the property that each sub-group is representative in relation to each other sub-group and with respect to said initial file of data;

constructing a model which establishes a mathematical relationship between said numerical initial data and said corresponding value of said physical quantity which is known for each of said plurality of model products;

validating said model;

feeding said at least one measuring device with said desired product;

measuring a plurality of sample measured values of said physical quantity on said at least one measuring device for said desired product to produce sample data;

recording said sample data; and applying said model for said sample data to determine said value of said physical quantity for said desired product.

2. A process according to claim 1 wherein:

said step of successively measuring said model measured value includes submitting said numerical initial data of said initial file to a mathematical transformation, and said step of distributing includes choosing a number of sub-groups greater than or equal to two, choosing a size of each of said sub-groups, generating at least one initial distribution of the numerical initial data among said sub-groups, evaluating the quality of the at least one initial distribution of the numerical initial data into sub-groups on the basis of at least one quality criterion, selecting a selected distribution to be modified in the next step in the case of a plurality of initial distributions, generating a new distribution by modifying said selected distribution of the numerical initial data among the sub-groups according to an optimization technique, evaluating the quality of said new distribution on the basis of said at least one quality criterion to produce a value of the quality of said new distribution, iteratively repeating said steps of selecting a selected distribution, generating a new distribution, and evaluating the quality of the new distribution until satisfaction of a stopping criterion obtained by comparing said value of said quality of said new distribution with a fixed threshold or until the number of iterations reaches a fixed maximum number.

3. A process according to claim 2 wherein said quality criterion consists of at least one criterion chosen from the following:

criterion of representativity of the numerical initial data of said sub-groups with respect to the measured quantity, which employs a metric characterizing a distance between said sub-groups, criterion of homogeneity serving to compare between them on the one hand the shapes and on the other hand the orientations of said sub-groups, criterion of homogeneity serving to compare between them the densities of the numerical data in said sub-groups.

4. A process according to claim 2 or 3 wherein said optimization technique consists of at least one method chosen from the following:

method which employs at least one genetic algorithm, method which employs at least one neural network, method which employs at least one simulated annealing algorithm, incremental method, method which employs at least one matrix criterion of optimality, and iterative method of the bootstrap type.

5. A process according to one of claims 2 or 3 wherein said choice of said size of said sub-groups is optimized by applying a method of iterative optimization of a quality criterion.

* * * * *